United States Patent [19]
Butler

[11] Patent Number: 5,162,874
[45] Date of Patent: Nov. 10, 1992

[54] ELECTROPHOTOGRAPHIC MACHINE HAVING A METHOD AND APPARATUS FOR MEASURING TONER DENSITY BY USING DIFFUSE ELECTROMAGNETIC ENERGY

[75] Inventor: Michael A. Butler, Rochester, N.Y.
[73] Assignee: Xerox Corporation, Stamford, Conn.
[21] Appl. No.: 632,897
[22] Filed: Dec. 24, 1990
[51] Int. Cl.$^5$ .......................................... G01N 21/47
[52] U.S. Cl. ................... 356/446; 356/445; 355/246; 355/203; 250/358.1; 250/341
[58] Field of Search ............... 356/446, 319, 320, 323, 356/246, 445; 250/358.1, 341, 353

[56] References Cited

U.S. PATENT DOCUMENTS

| | | | |
|---|---|---|---|
| 4,239,372 | 12/1980 | Iwai | 355/14 R |
| 4,273,843 | 6/1981 | Fujita et al. | 430/30 |
| 4,318,610 | 3/1982 | Grace | 355/14 D |
| 4,372,672 | 2/1983 | Pries | 355/14 R |
| 4,377,338 | 3/1983 | Ernst | 355/14 D |
| 4,451,135 | 5/1984 | Okumura | 355/3 DD |
| 4,462,680 | 7/1984 | Ikeda | 355/14 D |
| 4,502,778 | 3/1985 | Dodge et al. | 355/14 E |
| 4,551,004 | 11/1985 | Paraskevopoulos | 355/3 DD |
| 4,552,780 | 11/1985 | Abe et al. | 427/8 |
| 4,553,033 | 10/1985 | Hussle, III et al. | 356/445 |
| 4,676,653 | 6/1987 | Strohmeier et al. | 356/446 |
| 4,729,657 | 3/1988 | Cooper et al. | 356/319 |
| 4,796,065 | 1/1989 | Kanbayashi | 355/14 E |
| 4,799,082 | 1/1989 | Suzuki | 355/14 R |
| 4,801,980 | 1/1989 | Arai et al. | 355/14 D |
| 4,837,597 | 6/1989 | Bisaiji | 355/203 |
| 4,950,905 | 8/1990 | Butler et al. | 250/358.1 |
| 5,053,822 | 10/1991 | Butler | 356/446 |

OTHER PUBLICATIONS

Xerox Patent Appln. Ser. No. 07/399,051 (D/89036) filed on Aug. 25, 1989 for Hubble III et al.
Xerox Patent Appln. Ser. No. 07/398,597 (D/89035) filed on Aug. 25, 1989 for Hubble III et al.
Xerox Patent Appln. Ser. No. 07/246,242 (D/87214) filed Sep. 19, 1988 for Hubble III et al.

*Primary Examiner*—Vincent P. McGraw
*Assistant Examiner*—LaCharles P. Keesee
*Attorney, Agent, or Firm*—Denis A. Robitaille

[57] ABSTRACT

An electrophotographic apparatus having a densitometer, which measures material density located on a substrate by detecting and analyzing only a single diffuse electromagnetic energy signal reflected off of the density of material located on the substrate. Specifically, the apparatus must first be compensated for environmental and individual machine differences using a high density of the material. Moreover, once compensated, the apparatus is calibrated to determine the relationship between diffuse signals and material density. This relationship is calculated by sampling a clean substrate and low densities of the material. Once the relationship is determined, densities of material can be calculated given a corresponding diffuse signal. The calibrated and compensated density calculations enable accurate monitoring and adjustment of the electrophotographic apparatus color toner development systems.

26 Claims, 4 Drawing Sheets

ELECTROPHOTOGRAPHIC MACHINE HAVING A METHOD AND APPARATUS FOR MEASURING TONER DENSITY BY USING DIFFUSE ELECTROMAGNETIC ENERGY

BACKGROUND OF THE INVENTION

1. Field of the Invention

The present invention relates generally to an electrophotographic machine. Specifically, there is provided an improved method and apparatus which improves high toner density measuring by using diffuse electromagnetic energy readings.

2. Description of the Prior Art

It is known in the copying art to use electromagnetic energy (light) sensors to measure the density of powderous or liquid substances. The following are examples of such devices.

For example, co-pending U.S. patent application Ser. No. 07/399,051, describes a densitometer which measures the reduction in the specular component of the reflectivity of a portion of a surface having a liquid color developer material deposited thereon. Collimated light rays, in the visible spectrum, are projected onto the portion of the surface having the liquid thereon. The light rays reflected from the portion of the surface having the liquid deposited thereon are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays.

Similarly, Co-pending U.S. patent application Ser. No. 07/398,597, which is herein incorporated by reference in its entirety, describes an infrared densitometer which measures the specular and diffuse reflectivity of a bare photoconductive surface and that of a test area developed with black toner particles. This information serves as reference values for determining the fractional area of the test area covered with colored toner particles as a function of the measured diffuse reflectivity of the test area developed with colored toner particles. This value is compared to a reference and an error signal is generated.

Similarly, Co-pending U.S. patent application Ser. No. 07/246,242, which is herein incorporated by reference in its entirety, describes an infrared densitometer which measures the reduction in the specular component of reflectivity as toner particles are progressively deposited on a moving photoconductive belt. Collimated light rays are projected onto the toner particles. The light rays reflected from at least the toner particles are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays.

U.S. Pat. No. 4,950,905, which is herein incorporated by reference in its entirety, discloses a color toner density sensor. In that patent, light is reflected from a toner predominantly by either scattering or multiple reflections to produce a significant component of diffusely reflected light. Moreover, part of the sensor is arranged to detect only diffusely reflected light, and another part is arranged to detect both diffuse and specularly reflected light. In operation, the diffusely reflected light signals are used to identify increasing levels of diffusely reflected light which in turn indicates an increased density of toner coverage per unit of area.

U.S. Pat. No. 4,837,597, discloses an apparatus for detecting image density in a multicolor developing device. The invention uses two detection modes, one for color toners and another for black toner. Moreover, a hollow cylindrical drum having two portions is located behind light transmissive photosensitive toner carrying layers. When using black toner, one portion of the drum is used; similarly, the other drum portion is used with the color toners. The drum portions assist in controlling the amount of reflected light impinging onto a photodetector during testing of the toner densities on the photosensitive toner carrying layers.

U.S. Pat. No. 4,801,980, discloses a toner density control apparatus having a correction process. The object of the invention is to prevent a decrease in the image density even when the toner density sensor is contaminated with the toner particles. This is achieved by detecting the degree of contamination and thereby adjusting the light intensity of the reflective LED light source accordingly.

U.S. Pat. No. 4,799,082, discloses a means for determining the quantity of light reflected from a toner image located on a substrate. Specifically, the improvement comprises a way for varying the wavelength of the light emitted or the sensitivity of the detector in response to the spectral reflectance of the toner being deposited onto the substrate.

U.S. Pat. No. 4,796,065, discloses an apparatus for detecting image density in an image-forming machine. Specifically, there are two sensors employed, one receives regular reflecting light, the other receives scattered light reflected from a reference toner image. The signals from each sensor are compared and a differential signal is produced. Upon presetting the difference signal to be nil for a predetermined image density, an increase or a decrease of the reference toner image will invite a change of plus/minus sign of the differential signal.

U.S. Pat. No. 4,729,657, discloses a method of calibrating reflectance measuring devices. Specifically, the method includes automatic gain or sensitivity setting capability. Offset reflectance and reflectance of a secondary reflectance standard for several wavelengths are calculated and stored in a memory of a reflectance measuring device. A secondary standard is mounted in the reflectance measuring device and reflectances at a selected wavelengths from the secondary standard are read prior to measurement of the reflectance of the test sample. The stored offset reflectance and secondary reflectance for the operational wavelength are used to calculate true reflectance of the test sample.

U.S. Pat. No. 4,676,653, discloses a method for calibrating the light detecting measuring apparatus and eliminating errors of measurement caused by variations of the emitter or of other electronic components. This is accomplished by using one light transmitter and two detectors. A first detector measures light that is diffusely reflected off of a sample. A second detector measures light that is emitted from the light transmitter. The second detector information is used to calibrate the apparatus and to eliminate errors of measurement caused by variations in the transmitter or other electronic components.

U.S. Pat. No. 4,552,780, describes a multi-layer coating method based on differential spectral reflectance. Specifically, the method comprises applying over a colored intercoat at low hiding, colored top coat at incomplete hiding, thereby obtaining a color very similar to that of a top coat applied at complete hiding power. Moreover, there is a way for determining an appropriate intercoat color for a given top coat color.

U.S. Pat. No. 4,551,004, describes a toner density sensor. Specifically, the apparatus includes an LED, a phototransistor, a beam splitter, and a lens disposed between the beam splitter and a photoreceptor surface to collimate the light beam between the lens and the surface. A portion of the light emitted from the LED is transmitted through the beam splitter and the lens to the surface. Collimated light is reflected from the surface back through the lens and reflected from the beam splitter to the phototransistor. The output signal from the phototransistor is independent of the distance of the lens from the surface, because of the incident and reflected collimated light. Alternately, a second lens is disposed between the beam splitter and the phototransistor to enhance overall resolution.

Another example is U.S. Pat. No. 4,502,778, which discloses digital circuitry and microprocessor techniques to monitor the quality of toner operations in a copier and take appropriate corrective action based upon the monitoring results. Patch sensing is used. Reflectivity signals from the patch and from a clean photoconductor are analog-to-digital converted and a plurality of these signals taken over discrete time periods of a sample are stored. The stored signals are averaged for use in determining appropriate toner replenishment responses and/or machine failure indicators and controls.

U.S. Pat. No. 4,462,680 discloses a toner density control apparatus which assures always the optimum toner supply and good development with toner, irrespective of the kind of original to be copied and/or the number of copies to be continuously made. The apparatus has a detector for detecting the density of toner. The quantity of toner supply is controlled using a value variable at a changing rate different from the changing rate of the density difference between the reference toner density and the detected toner density.

U.S. Pat. No. 4,451,135 discloses a toner density detecting device. Specifically, the device detects the toner density of a dry-type, two-component developer, including a transparent plate arranged to be brought into contact with the developer, a light source for projecting light toward the developer through the transparent plate, and a light receiving element for receiving light scattered by the developer through the transparent plate. The transparent plate is separated optically by cutting it along a plane bisecting the light source and the light receiving element. In such a construction, multiple reflections inside the transparent plate, which affects the resulting measurement, can be completely eliminated, and thus it is possible to detect the toner density in an accurate and uniform manner.

U.S. Pat. No. 4,377,338 discloses a method and apparatus for copier quality monitoring and control. Specifically, there is data correlated to the light reflectance of a maximum toned area and a minimum toned area which is recorded to establish standards for monitoring and controlling subsequent copier operation. A test pattern is imaged onto the photoconductor by controlled illumination levels in a series of steps with the detection of light reflectance from that pattern being subsequently compared to establish the maximum black and maximum white criteria for storage. Light reflected from cleaned photoconductor areas and subsequently established toner patches are then used to compare against the original test pattern reflectance data. Toner replenishment, controls, and machine function monitoring are all based on these recorded standards from the test pattern.

U.S. Pat. No. 4,372,672, discloses a self triggering quality control sensor. Specifically, there is a system for checking copy quality variables within an electrophotographic copier machine involving the production of a developed sample test area and a base reference test area on a photoreceptive surface. An optical transducer is used to view the test area and circuits are provided to produce an output signal indicative of quality. The circuit triggers itself by detecting a substantial change in transducer produced signal level when the sample test area is viewed, thus negating the requirement that the test circuits be operated under the control of the machine.

U.S. Pat. No. 4,318,610, discloses an apparatus which controls toner density by sampling two test samples. A first test is run with a large toner density, wherein a second test has a smaller density. Developer mixture concentration is regulated in response to the first test. Photoconductive surface charging is regulated in response to the second test.

U.S. Pat. No. 4,273,843, discloses an apparatus for and method of detecting toner density in electrophotographic copying machines. Specifically, there is invention detects toner in a multi-component developer in an electrophotographic copying machine. Detection is accomplished by utilizing a source of illumination for projecting light onto the developer, and providing a receiving element for measuring the intensity of light of a predetermined wavelength reflected from the developer. The predetermined wavelength is selected to maximize the intensity of reflected light in response to variations in toner density, and to be substantially independent of the reflection characteristics of the developer. The density of toner in the developer is varied by the addition of toner in response to the measured intensity of the received reflection of the predetermined wavelength of light.

U.S. Pat. No. 4,239,372, discloses an electrophotographic copying machine with a toner control means. Specifically, the toner is controlled in accordance with the voltage developed by the reflection of light from an indexing image developed on the photosensitive member before or behind the transferred developed image. Moreover, the same reflected light also detects the presence of an unseparated transferred sheet to stop the machine operation before jamming occurs.

U.S. Pat. No. 4,239,372, discloses an apparatus and method for measuring the ratio of triboelectric toner particle electrostatic charge to toner particle mass in an electrostatographic device. Specifically, the ratio of the toner particle charge to the toner particle mass is determined by combining a measurement of the difference between the electrostatic photoreceptor potential with a measurement of a difference in optical reflectance, both being in the presence and in the absence of charged toner particles. The measurement of the difference in the electrostatic potential of the photoreceptor provides a quantity proportional to the toner particle charge per unit area. The measurement of the difference in optical reflectance provides a quantity related to the toner mass per unit area, a quantity that is linear for low particle densities. Combining the two difference measurements provides a quantity proportional to the toner charge per toner mass. Moreover, there is a feed back control signal for maintaining the ratio of the toner particle charge to toner particle mass in an acceptable range. This range controls the ratio of the toner and carrier particles in the developer mixture.

U.S. Pat. No. 4,239,372, discloses an apparatus and method for eliminating interference errors in dual beam infrared reflection measurements on a diffusely reflecting surface by geometrical elimination of interference producing specularly reflected radiation components. Specifically, the invention utilizes geometrical arrangements of apparatus components for geometrical selection of only diffusely reflected radiation components and elimination of specularly reflected radiation components that would produce interference errors. A specific application of this measurement technique is in connection with a two-layer sheet-form product having a film of infrared radiation transmissive material formed on a substrate or base layer with the interface surface being diffuse. A radiation source forms and directs two beams of infrared radiation of discrete wavelengths in angularly incident relationship toward an exposed specular surface of the film producing reflective components at both the specular surface and the diffuse interface surface. Only diffusely reflected components of incident beams of radiation are detected by a radiation responsive sensor which is disposed in a particular geometrical arrangement such that only the diffusely reflected beam components are incident to a radiation receptor surface of the sensor. Thus, interference errors are eliminated as the specularly reflected beam components will not be incident to the receptor surface of the radiation sensors.

An ideal goal in electrophotography is to have the correct amount of toner deposited onto a copy sheet on a continuous basis. With poor toner development control two situations occur. First, concerning a variability of toner quantity applied, too little toner creates lighter colors, where too much color toner creates darker colors. Second, concerning the machine, too much toner development causes excess toner waste which both increases the expense of running the machine and causes excessive wear on certain parts of the machine. Machines that can achieve precise control of the toner development system will have a tremendous competitive edge.

Typically, an electrophotographic machine, or just machine, utilizes a toner monitoring system. Most commonly, as exemplified by the prior described patents, a densitometer is used to determine the quantity of toner applied in order to establish some feedback and control over the toner development. These inventions have been successful in several applications. However, prior toner monitoring systems have had difficulty in accurately measuring thick and dense toner densities, especially with color toners. Machines that produce color copies must produce toner densities that are dense and thick in order to produce the solid color areas typically produced.

In response to these problems, a need exists for a toner development monitoring system which can accurately monitor the dense toner densities of color toners.

As a result, the present invention provides a solution to the described problems and other problems, and also offers other advantages over the prior art.

SUMMARY OF THE INVENTION

One aspect of the invention involves an apparatus for determining the density of a material placed on a substrate from a measurement of light reflected therefrom where the reflected light has a total flux including a spectral component and a diffuse component. The apparatus includes means for generating a diffuse signal representative of the diffuse component of the measurement of light reflected from the material placed on the substrate, means for generating a compensation ratio, means for generating a compensated specular signal representative of the spectral component of the measurement of light reflected from the material placed on the substrate, means for determining the density of the material placed on the substrate, and means, responsive to the compensated spectral signal, for calibrating the determining means to provide an accurate density measurement in response to a diffuse component of reflected light.

A second aspect of the invention involves an electrophotographic printing machine including an apparatus for determining the density of a material placed on a substrate from a measurement of light reflected therefrom where the reflected light has a total flux including a spectral component and a diffuse component. The apparatus includes means for generating a diffuse signal representative of the diffuse component of the measurement of light reflected from the material placed on the substrate, means for generating a compensation ratio, means for generating a compensated specular signal representative of the spectral component of the measurement of light reflected from the material placed on the substrate, means for determining the density of the material placed on the substrate, and means, responsive to the compensated spectral signal, for calibrating the determining means to provide an accurate density measurement in response to a diffuse component of reflected light.

BRIEF DESCRIPTION OF THE DRAWINGS

In the drawings, like reference numerals indicate corresponding parts of preferred embodiments of the present invention throughout the several views, in which.

DETAILED DESCRIPTION OF THE PREFERRED EMBODIMENTS

I. Electrophotographic Printing Machine

Although specific terms are used in the following description for the sake of clarity, these terms are intended to refer only to the particular structure of the invention selected for illustration in the drawings, and are not intended to define or limit the scope of the invention.

Figure 1:
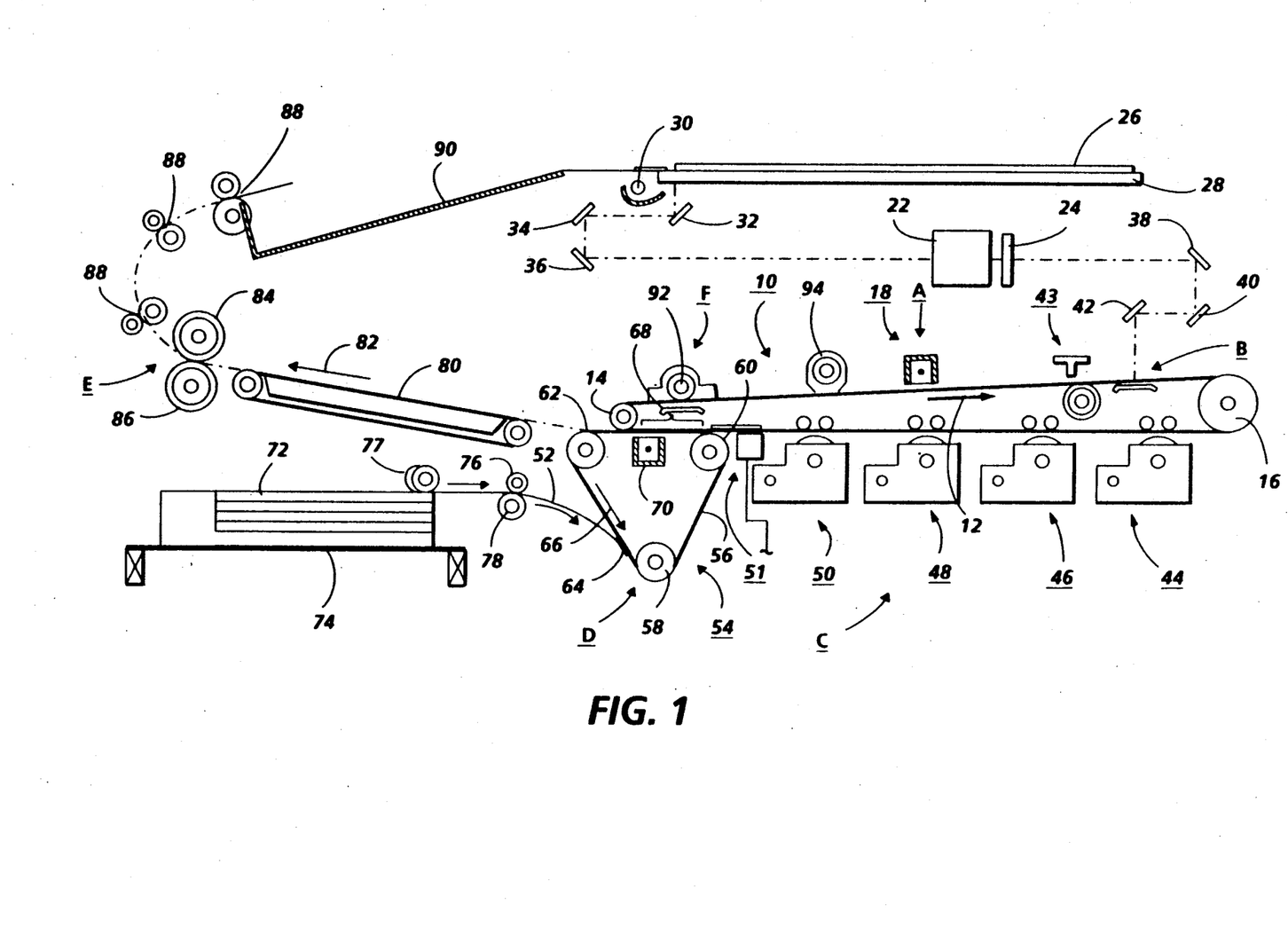
FIG. 1 is an electrophotographic color printing machine.

For a general understanding of the features of the present invention, reference is made to the drawings. In the drawings, like reference numerals have been used throughout to designate identical elements. FIG. 1 schematically depicts the various components of an illustrative electrophotographic printing machine incorporating the infrared densitometer of the present invention therein. It will become evident from the following discussion that the densitometer of the present invention is equally well suited for use in a wide variety of electrophotographic printing machines, and is not necessarily limited in its application to the particular electrophotographic printing machine shown herein.

Inasmuch as the art of electrophotographic printing is well known, the various processing stations employed in the FIG. 1 printing machine will be shown hereinafter schematically and their operation described briefly with reference thereto.

As shown in FIG. 1, the electrophotographic printing machine employs a photoreceptor belt 10, i.e. a photoconductive material coated on a grounding layer, which, in turn, is coated on an anti-curl backing layer. The photoconductive material is made from a transport layer coated on a generator layer. The transport layer transports positive charges from the generator layer. The generator layer is coated on the grounding layer. The transport layer contains small molecules of di-m-tolydiphenylbiphenyldiamine dispersed in a polycarbonate. The generation layer is made from trigonal selenium. The grounding layer is made from a titanium coated Mylar. The grounding layer is very thin and allows light to pass therethrough. Other suitable photoconductive materials, grounding layers, and anti-curl backing layers may also be employed. Belt 10 moves in the direction of arrow 12 to advance successive portions of the photoconductive surface sequentially through the various processing stations disposed about the path of movement thereof. Belt 10 is entrained about idler roller 14 and drive roller 16. Idler roller 14 is mounted rotatably so as to rotate with belt 10. Drive roller 16 is rotated by a motor (not shown) coupled thereto by suitable means such as a belt drive. As roller 16 rotates, it advances belt 10 in the direction of arrow 12.

Initially, a portion of photoconductive belt 10 passes through charging station A. At charging station A, a corona generating device, indicated generally by the reference numeral 18, charges photoconductive belt 10 to a relatively high, substantially uniform potential.

Next, the charged photoconductive surface is rotated to exposure station B. Exposure station B includes a moving lens system, generally designated by the reference numeral 22, and a color filter mechanism, shown generally by the reference numeral 24. An original document 26 is supported stationarily upon transparent viewing platen 28. Successive incremental areas of the original document are illuminated by means of a moving lamp assembly, shown generally by the reference numeral 30. Mirrors 32, 34 and 36 reflect the light rays through lens 22. Lens 22 is adapted to scan successive areas of illumination of platen 28. The light rays from lens 22 are transmitted through filter 24 and reflected by mirrors 38, 40 and 42 on to the charged portion of photoconductive belt 10. Lamp assembly 30, mirrors 32, 34 and 36, lens 22, and filter 24 are moved in a timed relationship with respect to the movement of photoconductive belt 10 to produce a flowing light image of the original document on photoconductive belt 10 in a non-distorted manner. During exposure, filter mechanism 24 interposes selected color filters into the optical light path of lens 22. The color filters operate on the light rays passing through the lens to record an electrostatic latent image, i.e. a latent electrostatic charge pattern, on the photoconductive belt corresponding to a specific color of the flowing light image of the original document. Exposure station B also includes a test patch generator, to provide toner test patches, indicated generally by the reference numeral 43, comprising a light source to project a test light image onto the charged portion of the photoconductive surface in the inter-image or inter-document region, i.e. the region between successive electrostatic latent images recorded on photoconductive belt 10, to record a test area thereon. It is noted that the test patch generator is not continuously operated. Toner test patches are only needed intermittently, to monitor the toner development. The test area, as well as the electrostatic latent image recorded on the photoconductive surface of belt 10, are developed with toner, either liquid or powderous, at the development stations (discussed later). A test patch is usually electrostatically charged and developed with toner particles to the maximum degree compatible with the dynamic range of the monitoring sensor so as to monitor as much of the process as practicable. Moreover, a separate test patch for each color toner is generated during operation.

After the electrostatic latent image and test area (or test patch) have been recorded on belt 10, belt 10 advances to development station C. Station C includes four individual developer units generally indicated by the reference numerals 44, 46, 48 and 50. The developer units 44, 46, 48 and 50 are of a type generally referred to in the art as "magnetic brush development units." Typically, a magnetic brush development system employs a magnetizable developer material including magnetic carrier granules having toner particles adhering triboelectrically thereto. The developer material is continually brought through a directional flux field to form a brush of developer material. The developer particles are continually moving so as to provide the brush consistently with fresh developer material. Development is achieved by bringing the developer material brush into contact with the photoconductive surface. Developer units 44, 46 and 48, respectively, apply toner particles of a specific color, which corresponds to the compliment of the specific color, onto the photoconductive surface. The color of each of the toner particles is adapted to absorb light within a preselected spectral reflection of the electromagnetic wave spectrum corresponding to the wave length of light transmitted through the filter. For example, an electrostatic latent image formed by passing the light image through a green filter will record the red and blue portions of the spectrums as an area of relatively high charge density on photoconductive belt 10. Meanwhile, the green light rays will pass through the filter and cause the charge density on the belt 10 to be reduced to a voltage level insufficient for development. The charged areas are then made visible by having developer unit 44 apply green absorbing (magenta) toner particles onto the electrostatic latent image recorded on photoconductive belt 10. Similarly, a blue separation is developed by developer unit 46, with blue absorbing (yellow) toner particles, while the red separation is developed by developer unit 48 with red absorbing (cyan) toner particles. Developer unit 50 contains black toner particles and may be used to develop the electrostatic latent image formed from a black and white original document. The yellow, magenta and cyan toner particles are diffusely reflecting particles. It is noted that the amount of toner deposited onto the photoconductive belt (or substrate) 10, is a function of the relative bias between the electrostatic image and the toner particles in the developer units. Specifically, a large bias will cause a proportionately larger amount of toner to be attracted to substrate 10 than a relatively smaller bias.

Each of the developer units 44, 46, 48 and 50 is moved into and out of an operative position. In the operative position, the magnetic brush is closely adjacent to belt 10, while, in the non-operative position, the magnetic brush is sufficiently spaced therefrom. During development of each electrostatic latent image, only one developer unit is in the operative position, the remaining developer units are in the non-operative position. This insures that each electrostatic latent image, and successive test areas, are developed with toner particles of the appropriate color without commingling. After being developed, a test patch passes beneath a densitometer, indicated generally by the reference numeral 51. Densitometer 51 is positioned adjacent the surface of belt 10. The test patch is illuminated with electromagnetic energy when the test patch is positioned beneath the densitometer. Densitometer 51, generates proportional electrical signals in response to electromagnetic energy, reflected off of the substrate and toner test patch, that was received by the densitometer. In response to the signals, the amount of developed toner mass per unit of area for each of the toner colors can be calculated. It should be noted, that it would be obvious to one skilled in the art to use a variety of electromagnetic energy levels for particular purposes. The detailed structure of densitometer 51 will be described hereinafter with reference to FIGS. 2 through 6, inclusive.

After development, the toner image is moved to transfer station D, where the toner image is transferred to a sheet of support material 52, such as plain paper among others. At transfer station D, the sheet transport apparatus, indicated generally by the reference numeral 54, moves sheet 52 into contact with belt 10. Sheet transport 54 has a pair of spaced belts 56 entrained about three rolls 58, 60 and 62. A gripper 64 extends between belts 56 and moves in unison therewith. Sheet 52 is advanced from a stack of sheets 72 disposed on tray 74. Feed roll 77 advances the uppermost sheet from stack 72 into a nip, defined by forwarding rollers 76 and 78. Forwarding rollers 76 and 78 advance sheet 52 to sheet transport 54 in synchronism with the movement of gripper 64. In this way, the leading edge of sheet 52 arrives at a preselected position to be received by the open gripper 64. The gripper 64 then secures the sheet thereto for movement therewith in a recirculating path. The leading edge of the sheet is releasably secured gripper 64. As the belts move in the direction of arrow 66, the sheet 52 moves into contact with belt 10, in synchronism with the toner image developed thereon, at transfer zone 68. Corona generating device 70 sprays ions onto the backside of the sheet so as to charge the sheet to the proper magnitude and polarity for attracting the toner image from photoconductive belt 10 thereto. Sheet 52 remains secured to gripper 64 so as to move in a recirculating path for three cycles. In this way, three different color toner images are transferred to sheet 52 in superimposed registration with one another. Thus, the aforementioned steps of charging, exposing, developing, and transferring are repeated a plurality of cycles to form a multi-color copy of a colored original document.

After the last transfer operation, grippers 64 open and release sheet 52. Conveyor 80 transports sheet 52, in the direction of arrow 82, to fusing station E where the transferred image is permanently fused to sheet 52. Fusing station E includes a heated fuser roll 84 and a pressure roll 86. Sheet 52 passes through a nip defined by fuser roll 84 and pressure roll 86. The toner image contacts fuser roll 84 so as to be affixed to sheet 52. Thereafter, sheet 52 is advanced by forwarding roll pairs 88 to catch tray 90 for subsequent removal therefrom by the machine operator.

The last processing station in the direction of movement of belt 10, as indicated by arrow 12, is cleaning station F. A rotatably mounted fibrous brush 92 may be positioned in cleaning station F and maintained in contact with belt 10 to remove residual toner particles remaining after the transfer operation. Thereafter, lamp 94 illuminates belt 10 to remove any residual charge remaining thereon prior to the start of the next successive cycle.

II. Densitometer Background

Figure 2:
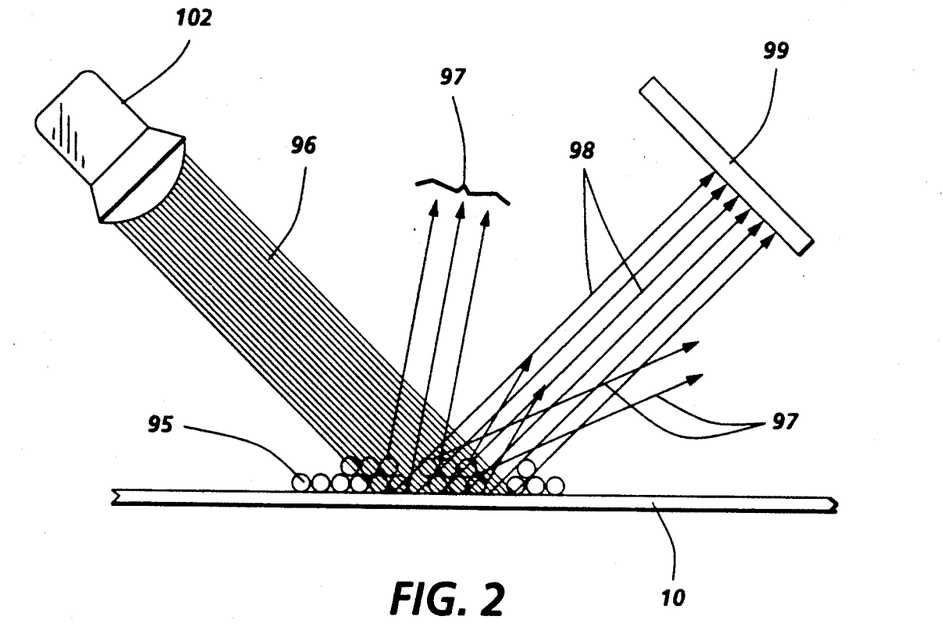
FIG. 2 is a schematic of a simplified densitometer.

Turning to FIG. 2, the following is a review of the principles of operation of a typical toner density sensor. Toner 95 is illuminated with a collimated beam of light 96 from an infrared LED (light emitting diode) 102. It is possible to discuss the interaction of this light beam with the toned photoreceptor sample with three broad categories. A portion of the light reflected by the sample is captured by light receptor 99. There is light that is specularly reflected, generally referred to as specular light component 98, from the substrate or photoreceptor belt 10. This is light that obeys the well known mechanisms of Snell's law from physics; the light impinging upon the surface is reflected at an angle equal to the angle of incidence according to the reflectivity of that surface. For a complex, partially transmissive substrate, the specularly reflected light may result from multiple internal reflections within the body of the substrate as well as from simple front surface reflection. Thus, an appropriately placed sensor will detect the specular light component. However, not all light will be specularly reflected. The second light component, known as diffuse light component 97, is near to isotropically reflected over all possible angles. The light can be reflected as a result of either single or multiple interactions with both the substrate 10 and toner particles 95. Diffusely reflected light is scattered by a complex array of mechanisms. Finally, there is light that, by whatever mechanism, leaves this system of toned photoreceptor sample and light detector. The light may be absorbed by the toner or the photoreceptor, or be transmitted through the sample to be lost to the system by the mechanisms of absorption or reflection. As a result of toner development onto substrate 10, the intensity of the light specularly reflected 98 from the substrate 10 is increasingly attenuated, yielding a smaller and smaller specular component of light. The attenuation is the result of either absorption of the incident light 96, in the case of black toners, or by scattering of the incident light 96 away from the specular reflection angle, in the case of colored toners. Thus, yielding a smaller specular light component being reflected off of substrate 10. It should be noted that it would be obvious to one skilled in the art to modify LED 102 to be most any electromagnetic energy source, and to modify toner 95 to be particles or liquid material.

Figure 3:
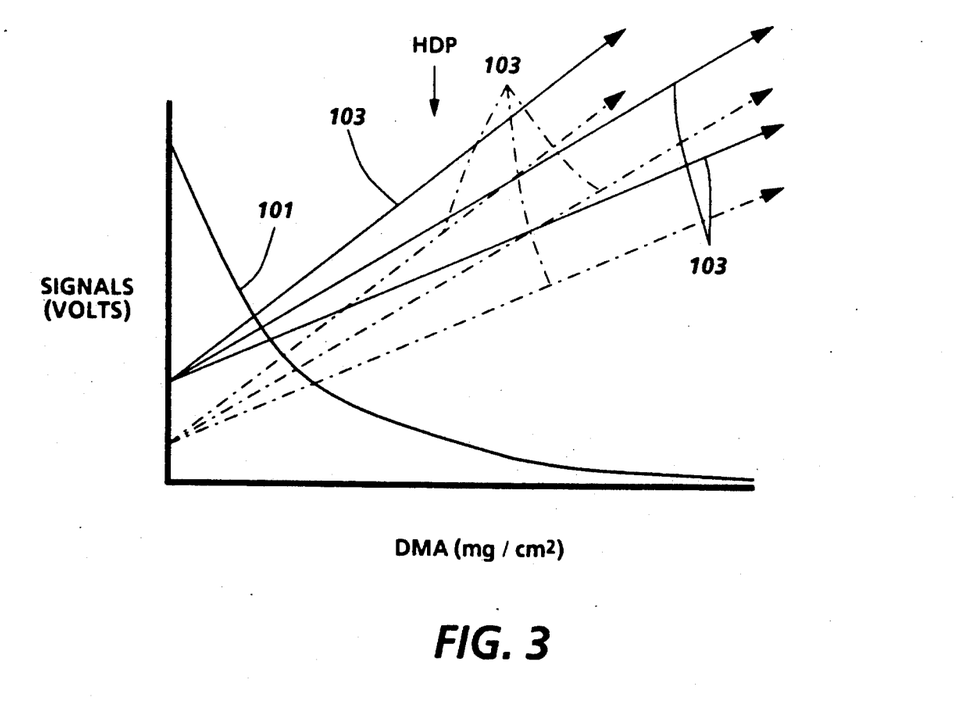
FIG. 3 is a graph showing specular reflection signal versus toner density mass per unit of area, and diffuse signal versus toner density mass per unit of area.

As shown by a graph in FIG. 3, and in reference to the other figures, there is a rough approximation of the specular-DMA relationship or curve. Specifically, there is a relationship between the DMA (developed toner mass per unit of area in mg/cm$^2$) and the specular light energy, or specular signal (measured in volts generated by the sensor), generally referenced by numeral 101. In particular, at a high DMA quantity, there is only a very small specular signal, since most of the incident light impinging onto the substrate is attenuated as discussed in relation to FIG. 2. Namely, the incident light is either scattered, thus becoming diffuse light in the case of color toner, or the incident light is mostly absorbed, in the case of black toner. Furthermore, the specular signal, in volts, will eventually become insignificantly small, since toner will eventually completely cover the substrate given enough DMA density. Additionally, as illustrated in the graph, at a low DMA quantity, there is a higher specular light signal voltage reading, since most of the incident light is specularly reflected off the substrate and less of the incident light is attenuated by the toner, as discussed concerning FIG. 2. It is noted here, that there is slight variation between different toner colors.

It is this specular-DMA relationship that has allowed for easy monitoring of DMA densities for black toners. Specifically, black toners only allow the sensor to collect light reflected from the substrate, since all light contacting the black toner is absorbed. As has been previously described, this absorption is not so for color toners, which creates difficulty in using the same techniques in monitoring color toner densities.

However, there are limitations in using the specular-DMA relationship. Specifically, specular signals are not responsive to both changing environmental conditions and differences between individual machines. Environmental conditions are defined as, for example, relative humidity, temperature, dirt build-up on the densitometer sensors, and electronic circuit drift. Similarly, differences between individual machines, for example, involves characteristic variability between sensors, static and dynamic variations in mounting distances or angle settings of the sensor, and variability between photoreceptors and similar image bearing members; simply put, no two machines are alike. It is obvious to one skilled in the art, that these factors are responsible for skewing the readings from feedback toner monitoring control systems, which in effect, are directly responsible for regulating the amount of toner deposited on copy sheets.

Nevertheless, there is a way to compensate for the changing environmental conditions and the variable characteristics between individual machine component limitations which effect the specular-DMA relationship. This way of compensation will be discussed latter in section three.

However, there is one limitation of the specular-DMA relationship that can not be compensated for. Namely, the specular signal is not accurate for high DMA densities, around HDP (high density patch) and above. Specifically, the specular signal becomes too small to accurately measure the DMA well before the HDP density is achieved. Significantly, an HDP density is required for many color patches. HDP is the threshold DMA density required for a complete coverage of substrate 10, also often referred to as a full density patch. In effect, by achieving an HDP or higher, a solid color picture is achieved on a copy sheet. The requisite DMA for an HDP is usually around a quantity of 0.78 mg/cm$^2$. The exact value of the DMA is primarily a function of the particle size of the toner and to a minor extent the reflectivity of the underlying substrate. It is found for all cases of interest that as the toner particle size varies, the DMA of the HDP scales in a manner proportional to changes in the maximum DMA required for printing.

As a result of the specular signal's uncompensatable limitation, the diffuse signal is desirable to use in determining DMA densities approaching HDP densities and beyond. As illustrated in FIG. 3, there is a rough approximation of the diffuse-DMA relationship or curve, generally referred to by the various reference numerals 103. Specifically, this relationship is between diffuse light energy (also referred to as a diffuse signal measured in volts), and DMA densities (mg/cm$^2$). As illustrated, the diffuse-DMA relationship is illustrated as being a substantially straight linear relationship. However, this is only a simplification, or approximation of the diffuse-DMA curve. There is, in actuality, some curvature to the diffuse-DMA curve. However, the approximation is easier to determine and adequate for determining DMA from the diffuse signals in order to monitor and adjust the toner developing system. However, if a plurality of DMA-diffuse readings were analyzed a more precise curve or relationship would be possible.

Concerning the diffuse-DMA curve, it is noted that there is a diffuse signal from a clean photoreceptor, a zero DMA density value. This signal results since almost all surfaces have deformities causing scattering of the reflected electromagnetic (light) energy impinging thereon.

A specific problem with the diffuse-DMA curve 103, as illustrated by the several curves drawn, is that the exact slope of the diffuse-DMA curve 103 is difficult to determine. Namely, there are many variables that may affect the diffuse-DMA curve 103. Specifically, the slope is affected by the many differences between different machines, such as the distance that the sensor lies from the substrate, or the reflective characteristics of individual substrates. Moreover, even the size of the toner particles used for each color or from one batch of toner to the next can affect the diffuse curve characteristics. Nevertheless, the ability to measure DMA before and well beyond the HDP densities makes the diffuse-DMA relationship 103 desirable to use. It is noted that there is diffuse sensitivity ranging up to 2.0 to 5.0 mg/cm$^2$, depending upon toner characteristics, after these densities the diffuse signal becomes relatively a constant value. However, most full density color developed areas utilize densities around 1.0 mg/cm$^2$, well before the diffuse signal becomes constant.

It is the subject of this invention to overcome the unpredictableness of the diffuse-DMA relationship by using the compensated predictable specular signal relationship as a guide post. Specifically, by taking two or more compensated specular readings of different low DMA densities (below 0.78 mg/cm2) the diffuse-DMA relationship can be calibrated. In particular, by taking at least diffuse and specular readings of a clean substrate (0.0 mg/cm$^2$), and an intermediate DMA density (between 0.0 mg/cm$^2$ and 0.78 mg/cm$^2$) the approximate relationship between diffuse signals and DMA densities can be determined since the slope of the line (relationship) would then be known and at least two points on the diffuse-DMA curve is known, which allows for extrapolation to determine an accurate diffuse-DMA relationship. This process is further discussed subsequently.

III. Determination of an Uncompensated Specular Value

Figure 4:
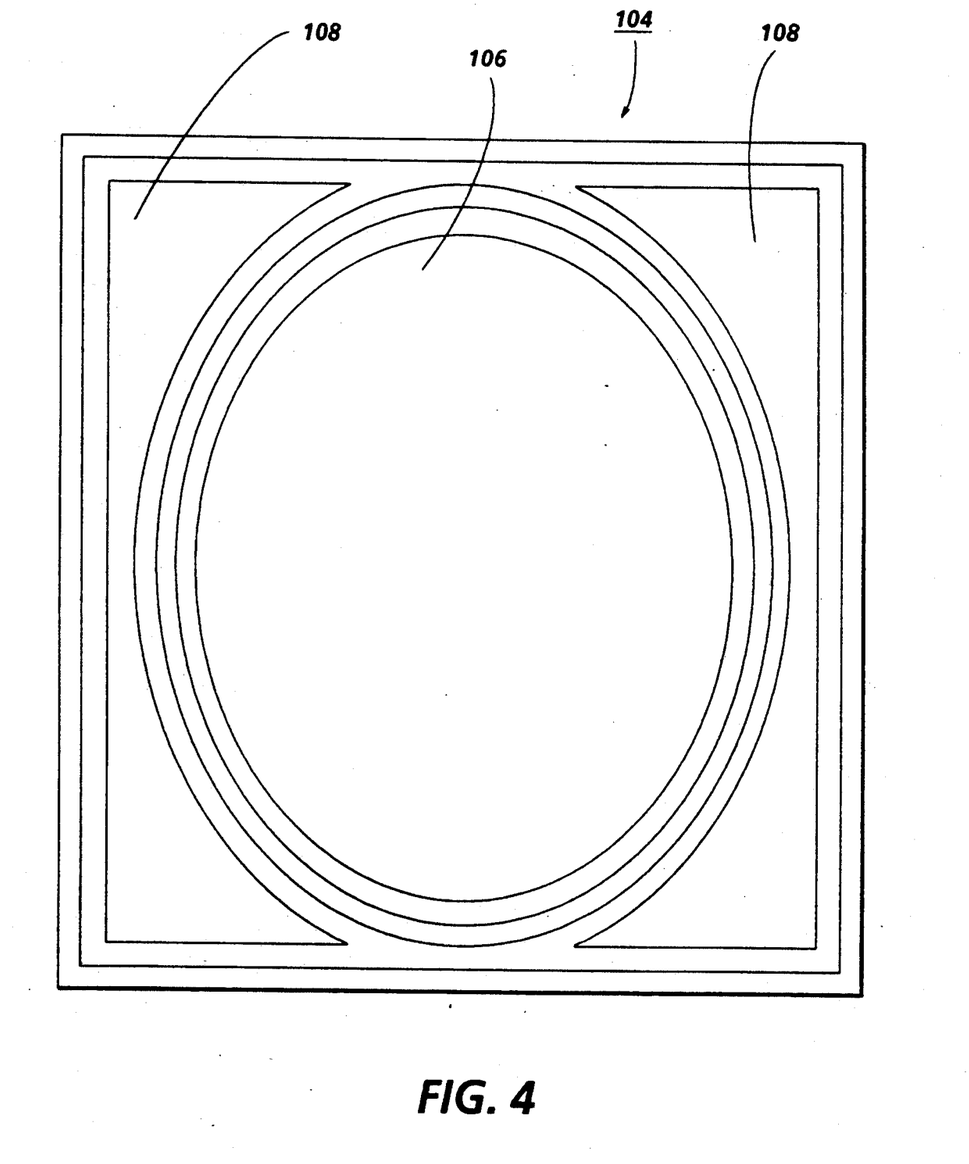
FIG. 4 is a representation of a toner area coverage sensor.

Before the specular and diffuse signals can be utilized, they first must be identified; a sensor, as illustrated in FIG. 4, is used to do just that. In FIG. 4, there is shown a toner area coverage sensor, generally referred to as sensor 104, which is used in the present invention. Sensor 104 uses a large aperture (not shown) relative to the incident beam spot size, this achieves greater mounting latitude (placement of the sensor in a proper coordinate location and with proper parallelism with respect to the photoreceptor). As a consequence, when used with color toners, central light reflection detector 106 (also referred to as the central detector) collects both specular and diffuse light components, or referred to as the total light flux. At most color toner DMA densities, a sensor which only measures total light flux degrades sensitivity and accuracy as a result of the increased percentage of diffusely reflected light which is also collected onto a single sensor. Specifically, as described in FIG. 3, the specular light signals, which indicate the lower DMA densities easily, will now be distorted by the diffuse light components. To remedy this specular-diffuse mixing situation, sensor 104 has an additional photodiode detector, which collects only the diffusely reflected light component, referred to as periphery detector 108. The advantage of the additional detector arrangement allows for separation of the specular light component from the total flux light component collected by the central detector. Specifically, in operation, the specular value or signal ($S_{LD}$) for a low density toner patch is determined by:

$$S_{LD} = T_{LD} - D_{LD}$$

Where, the diffuse signal ($D_{LD}$) is subtracted from the total flux detector signal ($T_{LD}$) which has both specular and diffuse light components. Thus, the true specular signal $S_{LD}$ can be determined. This equation is an approximation for low density, as indicated in FIG. 3. Thus, the "LD" subscripts indicate "low density." Additionally, this equation is based on the assumption that diffusely reflected light is evenly distributed over the whole sensor 104, and that there is consideration for the areas of the sensors to be equated. One such sensor that operates in the above described fashion is previously described co-pending U.S. patent application Ser. No. 07/246,242, which was incorporated by reference. Another such sensor which operates in the above described fashion is described in U.S. Pat. No. 4,950,905, which was previously incorporated by reference in its entirety. It is noted that other arrangements of sensors will also work; such as an array of small light detectors as provided by a charge-coupled device (CCD) or the like.

IV. Densitometer Operation Using A Specular Value Compensation Factor

As has been discussed previously, the prior specular signal calculations have not been responsive to both changing environmental conditions and differences between individual machines. As you will recall, for example, dust conditions in and on the densitometer are a changing environmental condition. To one skilled in the art, it is known that dust does not accumulate evenly on all objects; specifically, it has been found that dust can accumulate very unevenly upon lenses of a densitometer. For example, dust has been found to accumulate in a line running substantially over detector 106. If a densitometer does not take this environmental condition into account, the wrong DMA concentration will be calculated which will lead to improper adjustment of toner development. Specifically, signal $T_{LD}$ will be lower as a result of the environmental dust condition, yet signal $D_{LD}$ remains the same (relatively higher). Therefore, a lower $S_{LD}$ signal value will be calculated and used to adjust the toner development system to develop with a lower DMA density than is required.

Referring to FIGS. 2-4, the current invention has proposed to incorporate a compensation ratio, referred to as R, into the specular-DMA relationship calculation. To calculate 'R,' a high density DMA patch (HDP) is placed onto the substrate 10. Where a high density DMA patch is greater than the minimum value required to reduce the specular signal to a negligible value. As described earlier, a typical minimum value for the DMA may be 0.78 mg/cm². Next, the HDP is illuminated via a light source. Sensor 104 receives the light reflected off of the substrate 10 and HDP and generates two signals. One signal, being a high density total light flux signal ($T_{HD}$) generated by detector 106; the other signal being a high density diffuse light signal ($D_{HD}$) generated by detector 108. A ratio of these two signals, total light flux signal divided by the diffuse light signal, will yield the compensation ratio. For example, under typically ideal conditions, as discussed in reference to FIG. 3, DMA concentrations around 0.78 mg/cm² and greater should result in an insignificant specular light component and a large diffuse light component. Thus, the central detector signal ($T_{HD}$) will only be a diffuse light component, for demonstrating purposes lets call it value x. Moreover, the periphery detector ($D_{HD}$) also is the diffuse light component, having the same value x. By taking a ratio of the two detector signals under "ideal conditions" the ratio should be equal to one.

$$T_{HD} = x$$

$$D_{HD} = x$$

$$R = T_{HD}/D_{HD} = X/X = 1.$$

Now, under "normal operating conditions," it is understood that the compensation ratio will most likely not be equal to one. Specifically, ratio R will vary depending upon the changing environmental conditions and differences between individual machines. For example, take the dirt deposit discussed earlier. Dirt located on the central detector will decrease the signal received by the central detector which is the numerator in the ratio; thus lowering the value of R. A more complete discussion of an application of this variability follows. It is noted that for any DMA density over HDP, calculation of the compensation ratio R will result in a constant value.

Once R is calculated, the machine is now ready for standard operation in determining low DMA densities from a true value of the specular signal $S_{LD}$, where subscripted LD indicates low density, defined as a DMA concentration equal to or lower than 0.78 gm/cm². The use of a lower DMA is important, as discussed over FIG. 3, since both specular and diffuse light components may be sensed by the densitometer.

Unlike the high density material (toner) test runs, the central detector value ($T_{LD}$) is expected to be different than the periphery detector value ($D_{LD}$) since there is a specular light component added to the central detector 106. In operation, the compensation ratio R is incorporated into the compensated calculation as follows:

$$T_{LD} - ((R)(D_{LD})) = S_{LD}.$$

Therefore, with this compensated calculation, a true value of the specular signal $S_{LD}$ can be more accurately calculated. Consequently, a reliable DMA value can be calculated from the compensated specular signal ($S_{LD}$).

Referring back to the dirt calculation discussion, the R ratio would have a value less than one since the central detector was not receiving the full expected value. Similarly, the central detector's signal $T_{LD}$, in the second test run, will also have a lower signal than what it should have under ideal (clean) conditions. Similarly, the periphery detector's signal $D_{LD}$ will proportionately be too high in comparison to the degraded central detector signal. However, by using the compensated calculation, $D_{LD}$ will be lowered by the compensation ratio value of R (being less than one). Therefore, a true specular signal $S_{LD}$ is calculated, and more significantly, the true DMA concentration is accurately identified from the specular-DMA relationship, which in turn allows for proper calculation of the diffuse-DMA relationship.

One skilled in the art will appreciate that this compensation calculation will work for all of the above described changing environmental conditions and differences between individual machines which are related to the densitometer and marking particle development. This compensation R value is accomplished since we know that the specular signal is diminished essentially to zero and the calculation of the ratio R becomes constant for all DMA values greater than the minimum HDP value. Furthermore, any variation in this expected test will be accounted for in the compensation ratio which will adjust the calculation of actual specular light component calculation in subsequent test patch runs.

It is noted that, only one toner color (excluding black) is required to determine what the compensation factor R should be for all applications in a given time period. This factor R compensates for deficiencies in the sensor 104. Thus, once adjusted, the sensor 104 is accurate for future uses, regardless of the different hues of material.

Concerning the timing of the compensated specular signal and the compensation ratio, one skilled in the art will appreciate that there are many variations on when these operations may be executed. For example, the ratio could be calculated once a day when the machine is activated in the morning, or calculated after a certain number of copy sheets have been created, or even every time the toner development system is activated. Moreover, for example, the compensated specular signal could be calculated anywhere from every toner development use (given appropriate circuitry or potentially a second detector arrangement to measure only the HDP developed beside the low density patch), or spacing the calculations out over the use of the machine over an hourly or per count basis.

V. Densitometer Circuitry and Operation

Figure 5:
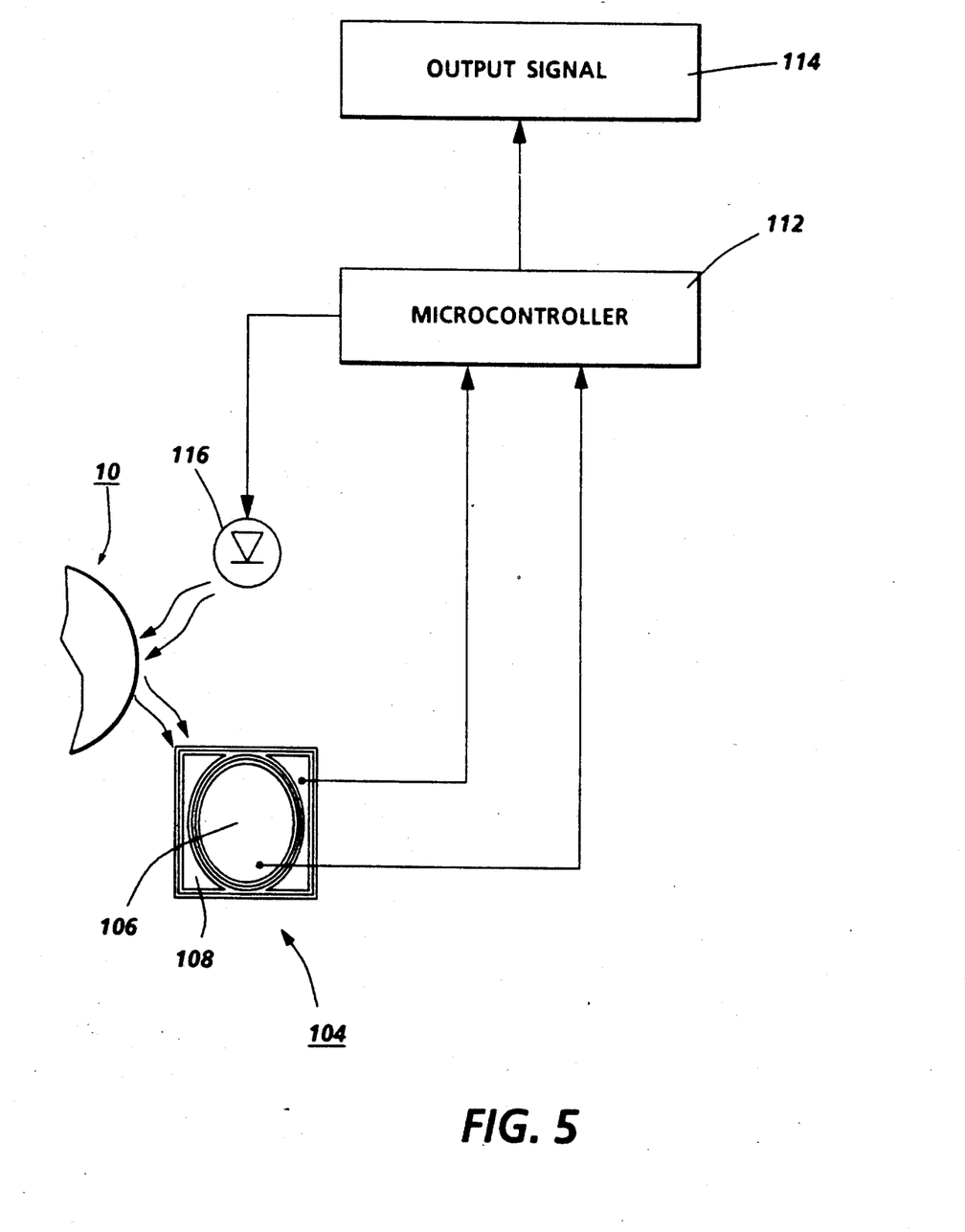
FIG. 5 illustrates an electronic diagram for the apparatus.

Turning now to FIG. 5, and referring to the other figures as well, there is a representation of the densitometer electronic circuitry. As shown, there is a microcontroller 112, output signal 114, LED 116, substrate 10, detector 104, central sensor 106, and periphery detector 108. Microcontroller circuitry block 112, represents appropriate circuitry comprising analog to digital circuitry, digital to analog circuitry, ROM and RAM components, bus circuits, as well as the circuitry for timing of the activation between the components in the microcontroller circuitry and the components connected to the microcontroller circuitry shown in the figure, as well as other appropriate components.

The following is a description of the process, in relation to the circuitry, for determining the diffuse-DMA relationship. For simplicity, only the process for determining one color toner DMA will be described, since determining the other color DMAs will incorporate the same process. Although, it is noted, each color toner may have different specular-DMA curves, and that these would all be accounted for.

First, there is the operation of determining the compensation factor R in relation to the circuitry. First, the toner development system is activated to develop a high density patch (HDP) onto substrate 10. Next, LED 116 is activated when the HDP is positioned to receive the incident light from LED 116. Next, central and periphery detectors 106 and 108 receive reflected light from the toner and substrate 10. Then, total flux ($T_{HD}$) and diffuse ($D_{HD}$) component signals are generated. These, signals are sent to microcontroller 112, where the compensation factor signal, $R = T_{HD}/D_{HD}$, is calculated and stored in microcontroller 112 for use in successive specular-DMA relationship calculations.

After determining the compensation ratio, the ratio is used in the specular-DMA relationship to calibrate the diffuse-DMA relationship. First, the toner development system, as previously described in FIG. 1, is activated by microcontroller 112 to develop a clean (zero mg/cm² of DMA) toner test patch onto substrate 10. Next, LED 116 is activated, by microcontroller 112, when the patch is positioned to receive the incident light from LED 116. Subsequently, central and periphery detectors, 106 and 108, receive reflected light from the toner and substrate 10. In response thereto, proportional signals are generated; from central detector 106, a first total flux signal ($T_1$), and from detector 108, a first diffuse light component signal ($D_1$). Thereafter, these first signals are sent to microcontroller 112, where a first specular light component signal ($S_1$) is calculated as follows: $T_1 - ((R)(D_1)) = S_1$. The resultant compensated specular signal ($S_1$) will be used to determine the DMA density ($C_1$) for the clean test patch run. Specifically, the DMA value can be calculated on the basis of the known relationship of the specular signal versus DMA density discussed concerning FIG. 3. Moreover, this known relationship is stored (for example as a lookup table) in microprocessor 112 for determining the DMA density from the compensated specular signal value. Thereafter, this first point (first DMA density to first diffuse signal ($C_1$, $D_1$)) is stored.

Next, an intermediate toner development test patch is run. An intermediate toner test patch has a DMA density below the HDP density and higher than the clean test patch. This intermediate density is developed onto substrate 10. Again, detectors 106 and 108 generate proportional signals, diffuse light component signal $D_2$ and total flux signal $T_2$, from the light reflected off of substrate 10 and the intermediate test patch. These second signals, $T_2$ and $D_2$, are sent to microcontroller 112, which calculates the intermediate DMA density the same way the clean test patch DMA density was calculated. Namely, the compensated diffuse light component signal is subtracted from the total flux signal to determine the intermediate specular light component signal, $T_2-((R)(D_2))=S_2$. From this intermediate specular light component value $S_2$ the DMA value ($C_2$) can be calculated by comparison to the known specular signal versus DMA density relationship. Thereby, this second point (second DMA density to second diffuse signal ($C_2, D_2$) is stored for use in determining the diffuse signal versus DMA relationship.

The final step, in determining the diffuse-DMA density relationship, is to set up the equation representing this approximate relationship from the two points previously calculated. Specifically, given two points, a slope can be calculated for the linear relationship. The approximation equation is as follows:

$$C_3 = C_1 + ((D_3 - D_1)(C_2 - C_1))/(D_2 - D_1)).$$

Where, any subsequent toner test patch DMA density quantity, $C_3$, can be determined from the diffuse signal, $D_3$, generated in response to that subsequent toner density test patch. Moreover, as noted earlier, if a multiplicity of low density DMA test patches were analyzed, then a more specific equation could be developed showing the slight curvature of the diffuse-DMA curve. It is noted, that all of these calculations are performed in the microcontroller 112.

Hereinafter, subsequent toner test patch DMA densities can be determined using diffuse sensor signals. Thus, typical full density color toner test patches can be used for determining proper adjustments to calibrate the toner development system. Specifically, a full toner density test patch is generated, a representative diffuse signal is created in response to the diffuse light reflected off the substrate and toner test patch which was thereby received by the sensor. Microcontroller 112 determines the corresponding DMA density for the full density patch. Now, appropriate output signals 114 are sent to adjust the electrophotographic machine to achieve proper DMA density ranges for the toner to be developed on a copy sheet based upon the full density color toner test patch. It is noted, once the machine has been calibrated from the specular signals, the diffuse signals will be sufficient to determine all DMA ranges, not just full density ranges.

It is to be understood, however, that even though numerous characteristics and advantages of the present invention have been set forth in the foregoing description, together with details of the structure and function of the invention, the disclosure is illustrative, and changes in matters of order, shape, size, and arrangement of parts may be made within the principles of the invention and to the full extent indicated by the broad general meaning of the terms in which the appended claims are expressed.

What is claimed is:

1. An apparatus for determining density of a material deposited on a portion of a substrate by measuring light reflected therefrom, the reflected light having a total flux including a spectral component and a diffuse component, comprising:
    means for generating a diffuse signal representative of the diffuse component of light reflected from the material placed on the substrate;
    means for generating a compensation ratio;
    means, responsive to the compensation ratio, for generating a compensated specular signal representative of the spectral component of the light reflected from the material;
    means, responsive to said diffuse signal, for determining the density of the material; and
    means, responsive to the compensated spectral signal, for calibrating said determining means.

2. The apparatus of claim 1 in which the substrate includes a high density portion having a high density of material deposited thereon, wherein said compensation ratio is a function of the diffuse component of the light reflected from the high density portion.

3. The apparatus of claim 1 in which the substrate includes a clean portion being substantially void of material deposited thereon, wherein said calibrating means comprises:
    first means for generating a clean total flux signal representative of a measurement of total light reflected from the clean portion on the substrate;
    first means for generating a clean diffuse signal representative of the diffuse component of light reflected from the clean portion on the substrate;
    first means for calculating a clean compensated specular signal as a function of the compensation ratio, the clean total flux signal, and the clean diffuse signal; and
    first means for determining a clean calibrated density measurement as a function of the clean compensated specular signal.

4. The apparatus of claim 3 in which the substrate includes a selected density portion having a selected density of material deposited thereon, wherein said calibrating means further comprises:
    second means for generating a selected density total flux signal representative of a measurement of total light reflected from the selected density portion on the substrate;
    second means for generating a selected density diffuse signal representative of the diffuse component of light reflected from the selected density portion on the substrate;
    second means for calculating a selected density compensated specular signal as a function of the compensation ratio, the selected density total flux signal, and the selected density diffuse signal; and
    second means for determining a selected density calibrated density measurement as a function of the selected density compensated specular signal.

5. The apparatus of claim 4, wherein said selected density is greater than zero density and less than said high density.

6. The apparatus of claim 4, wherein:
    said first determining means comprises a first electronic memory means having a first look-up table; and
    said second determining means comprises a second electronic memory means having a second look-up table.

7. The apparatus of claim 3, wherein said calibrating means comprises means for generating a linear equation approximating a relationship between the diffuse component of a measurement of light reflected from the substrate and the calibrated density measurement corresponding thereto.

8. The apparatus of claim 1, wherein said generating means includes microcontroller.

9. The apparatus of claim 8, wherein said microcontroller includes means for calculating the compensation ratio in accordance with the following equation:

$$R = T_{hd}/D_{hd},$$

where:
R represents the compensation ratio;
$T_{hd}$ represents the total flux signal representative of a measurement of total light reflected from an area on the substrate having a high density of material placed thereon; and
$D_{hd}$ represents the diffuse component of the measurement of light reflected from the area on the substrate having a high density of material placed thereon.

10. The apparatus of claim 8, wherein said microcontroller includes means for calculating a compensated specular signal representative of the specular component of a measurement of light reflected from the substrate in accordance with the following equation:

$$S = T - R(D)$$

where:
R represents the compensation ratio;
T represents the total flux signal representative of total light reflected from the substrate; and
D represents the diffuse signal representative of the diffuse component of the light reflected from the substrate.

11. The apparatus of claim 8, wherein said microcontroller includes means for calculating the calibrated density measurement in accordance with the following equation:

$$C_3 = C_1 + ((D_3 - D_1)(C_2 - C_1))/(D_2 - D_1)$$

where:
$C_3$ represents the calibrated density measurement corresponding to the measurement of reflected light;
$C_1$ and $C_2$ represent calibrated density measurements corresponding to measurements of reflected light having a predetermined density;
$D_3$ represents the diffuse component of the measurement of reflected light; and
$D_1$ and $D_2$ represent the diffuse components for the measurements of reflected light having a predetermined density.

12. The apparatus of claim 1, wherein said generating means includes an electromagnetic energy detector having periphery detector portion for sensing the diffuse component of the measurement of reflected light and a central detector portion for sensing the total flux of the measurement of reflected light.

13. The apparatus of claim 12, further including means for emitting light onto said substrate such that light reflected therefrom is received by said detector.

14. An electrophotographic printing machine including a development system having an apparatus for determining density of a material deposited on a portion of a substrate by measuring light reflected therefrom, the reflected light having a total flux including a spectral component and a diffuse component, comprising:
means for generating a diffuse signal representative of the diffuse component of light reflected from the material placed on the substrate;
means for generating a compensation ratio;
means, responsive to the compensation ratio, for generating a compensated specular signal representative of the spectral component of the light reflected from the material;
means, responsive to said diffuse signal, for determining the density of the material; and
means, responsive to the compensated spectral signal, for calibrating said determining means.

15. The apparatus of claim 14 in which the substrate includes a high density portion having a high density of material deposited thereon, wherein said compensation ratio is a function of the diffuse component of the light reflected from the high density portion.

16. The electrophotographic printing machine of claim 14 in which the substrate includes a clean portion being substantially void of material deposited thereon, wherein said calibrating means comprises:
first means for generating a clean total flux signal representative of a measurement of total light reflected from the clean portion on the substrate;
first means for generating a clean diffuse signal representative of the diffuse component of light reflected from the clean portion on the substrate;
first means for calculating a clean compensated specular signal as a function of the compensation ratio, the clean total flux signal, and the clean diffuse signal; and
first means for determining a clean calibrated density measurement as a function of the clean compensated specular signal.

17. The electrophotographic printing machine of claim 14 in which the substrate includes a selected density portion having a selected density of material deposited thereon, wherein said calibrating means further comprises:
second means for generating a selected density total flux signal representative of a measurement of total light reflected from the selected density portion on the substrate;
second means for generating a selected density diffuse signal representative of the diffuse component of light reflected from the selected density portion on the substrate;
second means for calculating a selected density compensated specular signal as a function of the compensation ratio, the selected density total flux signal, and the selected density diffuse signal; and
second means for determining a selected density calibrated density measurement as a function of the selected density compensated specular signal.

18. The electrophotographic printing machine of claim 17, wherein said selected density is greater than zero density and less than said high density.

19. The electrophotographic printing machine apparatus of claim 17, wherein:
said first determining means comprises a first electronic memory means having a first look-up table; and
said second determining means comprises a second electronic memory means having a second look-up table.

20. The electrophotographic printing machine of claim 16, wherein said calibrating means comprises means for generating a linear equation approximating a relationship between the diffuse component of a measurement of light reflected from the substrate and the calibrated density measurement corresponding thereto.

21. The electrophotographic printing machine apparatus of claim 14, wherein said apparatus includes microcontroller.

22. The electrophotographic printing machine of claim 21, wherein said microcontroller includes means for calculating a compensation ratio in accordance with the following equation:

$$R = T_{hd}/D_{hd},$$

where:

R represents the compensation ratio;

$T_{hd}$ represents the total flux signal representative of a measurement of total light reflected from an area on the substrate having a high density of material placed thereon; and $D_{hd}$ represents the diffuse component of the measurement of light reflected from the area on the substrate having a high density of material placed thereon.

23. The electrophotographic printing machine of claim 21, wherein said microcontroller includes means for calculating a compensated specular signal representative of the specular component of a measurement of light reflected from an area on the substrate in accordance with the following equation:

$$S = T - R(D)$$

where:

R represents the compensation ratio;

T represents the total flux signal representative of total light reflected from the substrate; and D represents the diffuse signal representative of the diffuse component of the light reflected from the substrate.

24. The electrophotographic printing machine of claim 21, wherein said microcontroller includes means for calculating the calibrated density measurement in accordance with the following equation:

$$C_3 = C_1 + ((D_3 - D_1)(C_2 - C_1))/(D_2 - D_1)$$

where:

$C_3$ represents the calibrated density measurement corresponding to the measurement of reflected light;

$C_1$ and $C_2$ represent calibrated density measurements corresponding to measurements of reflected light having a predetermined density;

$D_3$ represents the diffuse component of the measurement of reflected light; and $D_1$ and $D_2$ represent the diffuse components for the measurements of reflected light having a predetermined density.

25. The electrophotographic printing machine of claim 14, wherein said generating means includes an electromagnetic energy detector having a periphery detector portion for sensing the diffuse component of the measurement of reflected light and a central detector portion for sensing the total flux of the measurement of reflected light.

26. The electrophotographic printing machine of claim 25, further including means for emitting light onto said substrate such that light reflected therefrom is received by said detector.

* * * * *